United States Patent
Tipler et al.

(10) Patent No.: US 8,297,107 B2
(45) Date of Patent: Oct. 30, 2012

(54) SYSTEM FOR REGULATING FLUID FLOWING THROUGH CHROMATOGRAPHIC COLUMN

(75) Inventors: Andrew Tipler, Trumbull, CT (US); Richard G. Edwards, Brookfield, CT (US); Michael Paul Dinsmore, Berthoud, CO (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 11/751,327

(22) Filed: May 21, 2007

(65) Prior Publication Data

US 2007/0261474 A1    Nov. 15, 2007

Related U.S. Application Data

(63) Continuation of application No. 11/189,467, filed on Jul. 26, 2005, now Pat. No. 7,219,532.

(60) Provisional application No. 60/521,951, filed on Jul. 26, 2004, provisional application No. 60/657,210, filed on Feb. 28, 2005.

(51) Int. Cl.
    *G01N 30/04* (2006.01)
(52) U.S. Cl. .................................................... 73/23.42
(58) Field of Classification Search .................. 73/23.42
    See application file for complete search history.

(56) References Cited

U.S. PATENT DOCUMENTS

| | | | | |
|---|---|---|---|---|
| 4,484,483 | A | 11/1984 | Riegger et al. | 73/864.23 |
| 4,962,662 | A | 10/1990 | Berger | 73/23.42 |
| 4,994,096 | A * | 2/1991 | Klein et al. | 95/15 |
| 5,339,673 | A * | 8/1994 | Nakagawa et al. | 73/23.36 |
| 5,467,635 | A | 11/1995 | Nakagawa et al. | 73/23.35 |
| 5,476,000 | A * | 12/1995 | Henderson et al. | 73/23.27 |
| 5,524,084 | A * | 6/1996 | Wang et al. | 702/100 |
| 5,545,252 | A | 8/1996 | Hinshaw et al. | 95/15 |
| 5,670,707 | A | 9/1997 | Fennell et al. | 73/1 |
| 5,672,810 | A * | 9/1997 | Shibamoto | 73/23.25 |

(Continued)

OTHER PUBLICATIONS

F.R. Gonzalez et al. "Theoretical and practical aspects of flow control in programmed-temperature gas chromatography" Journal of Chromatography, Elsevier Science Publishers B.V. Amsterdam, NL, vol. 757, No. 1-2, Jan. 3, 1997, pp. 97-107.

(Continued)

*Primary Examiner* — John Fitzgerald
(74) *Attorney, Agent, or Firm* — St. Onge Steward Johnston & Reens LLC (57) ABSTRACT

Disclosed are systems and methods that include a sampling device, a chromatographic column, and a transfer line through which a fluid containing analytes to be measured are communicated from the sampling device to the column. The pressure at which the fluid containing the analytes is applied at the inlet of the transfer line is adjusted as the temperature of the column increases in accordance with certain relationships in order to maintain a substantially constant flow rate or velocity for the fluid exiting the column. In this way, the system compensates for changes in the viscosity of the fluid flowing through the column that result from changes in the column temperature.

9 Claims, 8 Drawing Sheets

U.S. PATENT DOCUMENTS

| | | | | |
|---|---|---|---|---|
| 5,711,786 | A | | 1/1998 | Hinshaw ............................ 95/82 |
| 5,767,387 | A | * | 6/1998 | Wang ............................ 73/23.42 |
| 5,782,964 | A | * | 7/1998 | Mustacich ...................... 96/102 |
| 6,652,625 | B1 | | 11/2003 | Tipler et al. ........................ 95/82 |
| 6,813,929 | B2 | | 11/2004 | Jochum, Jr. .................. 73/23.27 |
| 6,814,785 | B2 | | 11/2004 | Tipler et al. ..................... 96/105 |
| 7,219,532 | B2 | | 5/2007 | Tipler et al. .................. 73/23.42 |
| 2002/0194898 | A1 | | 12/2002 | Klee ............................. 73/23.35 |
| 2004/0020308 | A1 | | 2/2004 | Jochum, Jr. ................ 73/861.52 |
| 2005/0284209 | A1 | | 12/2005 | Tipler et al. .................. 73/23.42 |

OTHER PUBLICATIONS

R. Shellie, P. Marriott, P. Morrison, L. Mondello. "Effects of pressure drop on absolute retention matching in comprehensive two-dimensional gas chromatography" Journal of Separation Science, vol. 27, No. 7-8, May 7, 2004, pp. 504-512.

L.M. Blumberg. "Method Translation and Retention Time Locking in Partition GC" Analytical Chemistry, American Chemical Society. Columbus, US, vol. 70, No. 18, Sep. 15, 1998, pp. 3828-3839.

International Search Report, PCT, Oct. 17, 2005, 8 pages.

* cited by examiner

SYSTEM FOR REGULATING FLUID FLOWING THROUGH CHROMATOGRAPHIC COLUMN

RELATED APPLICATIONS

This is a continuation of U.S. patent application Ser. No. 11/189,467, filed Jul. 26, 2005, now U.S. Pat. No. 7,219,532, which claims priority benefits under Title 35, United States Code, Section 119(e), U.S. Provisional Patent Application No. 60/521,951, filed Jul. 26, 2004 and U.S. Provisional Patent Application No. 60/657,210, filed Feb. 28, 2005, the contents of each of which are herein incorporated by reference in their entirety.

FIELD OF THE INVENTION

The present invention relates to systems and methods for communicating a fluid containing analytes from a sampling device to a chromatographic column. More specifically, the invention relates to systems and methods in which the sampling device controls the fluid flowing through the column.

BACKGROUND OF THE INVENTION

Gas chromatography is essentially a physical method of separation in which constituents of a vapor sample in a carrier gas are adsorbed or absorbed and then desorbed by a stationary phase material in a column. A pulse of the sample is introduced into a steady flow of carrier gas, which carries the sample into a chromatographic column. The inside of the column is lined with a liquid, and interactions between this liquid and the various components of the sample—which differ based upon differences among partition coefficients of the elements—cause the sample to be separated into the respective elements. At the end of the column, the individual components are more or less separated in time. Detection of the gas provides a time-scaled pattern, typically called a chromatogram, that, by calibration or comparison with known samples, indicates the constituents, and the specific concentrations thereof, which are present in the test sample. An example of the process by which this occurs is described in U.S. Pat. No. 5,545,252 to Hinshaw.

Various types of sampling devices can be used to obtain a quantity of the analytes from the sample vessels used to collect the samples to be tested and transfer the analytes to the gas chromatograph for the above-described analysis. One common device is a thermal desorption unit, which is often employed to determine the constituents of a particular environment. For example, it is often desired to detect the amount of volatile organic compounds (VOCs) present in a certain sample of air. One way of doing this is by first transporting a tube packed with an adsorbent material into the environment to be tested, and allowing the VOCs in the air to migrate into the tube through natural diffusion, typically termed "diffusive" or "passive sampling." Alternatively, the VOCs may be collected by drawing a sample of gas (typically ambient air) through such a tube using a small vacuum pump, commonly referred to as "pumped sampling." In each case, the analytes to be measured (i.e., the VOCs) are retained by and concentrated on the adsorbent as the air passes through the tube.

Once the VOCs are collected in this fashion, the tube is then transported to a thermal desorption unit, where the tube is placed in the flow path of an inert gas, such as Helium or Nitrogen. The tube is subsequently heated, thereby desorbing the analytes, and the carrier gas sweeps the VOCs out of the tube. In some cases, a "trap" is located downstream of the sample tube in order to further pre-concentrate the analytes, and occasionally, remove moisture therefrom, prior to introducing the sample into the chromatographic column. One example is an adsorbent trap, usually cooled to a sub-ambient temperature, which is simply another sorbent tube packed with a suitable adsorbent material, which adsorbs the analytes as the sample gas first passes through the tube, and from which the analytes are then desorbed into the chromatographic column, usually by heating, for subsequent separation and analysis.

Another common sampling device is a headspace sampler. In conventional headspace sampling, sample material is sealed in a vial and subjected to constant temperature conditions for a specified time. Analyte concentrations in the vial gas phase should reach equilibrium with the liquid and/or solid phases during this thermostatting time. The vial is subsequently pressurized with carrier gas to a level greater than the "natural" internal pressure resulting from thermostatting and equilibration. Then the pressurized vial is connected to the chromatographic column in such a way as to allow for the transfer of a portion of the vial gas phase into the column for a short period of time. An example of such a sampling device is disclosed in U.S. Pat. No. 4,484,483 to Riegger et. al. An example of a chromatographic system employing a headspace sampler is disclosed in U.S. Pat. No. 5,711,786 to Hinshaw.

In some applications, the column is directly coupled to a sorbent tube in the sampling device or the device is connected to the column via a transfer line, such as, for example, via a length of fused silica tubing. Other recent applications employ an interface device for performing some additional control or trapping in addition to that already provided by the sampling device, including the thermal desorption system disclosed in U.S. patent application Ser. No. 11/169,935 to Tipler et al., as well as the headspace sampling system disclosed in U.S. Pat. No. 6,652,625 to Tipler, each of which is assigned to the assignee of the present application, and the contents of each of which are herein incorporated by reference in their entirety.

In some embodiments, however, as the column is heated, the viscosity of the gas flowing through it likewise increases. As a result, under isobaric conditions—where the carrier gas is applied at a constant pressure, the flow rate through the column will decrease. Though this has no detrimental effect on system performance in some applications, in other applications that employ a flow-sensitive detector, such as a mass spectrometer, the effect on performance can be dramatic.

Some gas chromatographs are equipped with programmable pneumatic controls, and thus, the chromatograph is able to compensate for such changes in gas viscosity by increasing the column inlet pressure at a rate calculated to maintain a constant flow rate through the column, which requires constant knowledge of the column temperature in order to calculate the viscosity at that temperate and make the appropriate adjustments to the applied pressure. However, this solution is not available when the gas pressure is controlled on a device remote from the chromatograph, such as on a thermal desorption unit or a headspace sampler, where the gas is supplied from the device along a transfer line and the remote device does not know the temperature of the column.

SUMMARY OF THE INVENTION

The present teachings include systems and methods for communicating a fluid containing analytes from a sampling device to a chromatographic column such that a substantially constant flow rate through the column is maintained as the column temperature changes. Further, systems and methods are provided for communicating a fluid containing analytes from a sampling device to a chromatographic column such that a substantially constant gas velocity in the column is maintained as the column temperature changes. Also, systems and methods are provided that minimize user input and human error.

To achieve at least some of the objects listed, the invention comprises a system for regulating fluid flowing through a chromatographic column, comprising a sampling device that supplies a carrier gas containing analytes to be measured and a gas chromatograph in fluid communication with the sampling device, where the chromatograph includes a chromatographic column that receives the carrier gas containing the analytes supplied by the sampling device and a temperature sensor connected to the sampling device that measures the temperature of the column and sends a signal to the sampling device indicating the measured temperature, wherein the sampling device controls the pressure of the carrier gas supplied to the column based on the signal received from the sensor.

In some embodiments, the sampling device adjusts the pressure of the carrier gas supplied to the column such that a substantially constant flow rate is maintained in the column. In some of these embodiments, the pressure of the carrier gas supplied to the column is calculated in accordance with the equation $$P_i = \sqrt{\frac{F_a \cdot T_t \cdot P_a}{a \cdot b \cdot T_a} \cdot \left(a \cdot \frac{T_c}{T_t} + b\right) + P_o^2}.$$

where $T_t$ is the transfer line absolute temperature, $T_c$ is the column absolute temperature, $T_a$ is the standard ambient absolute temperature, $P_o$ is the gas pressure at the column outlet, $P_a$ is the standard ambient pressure, and a and b represent $\pi d/256L\eta$ for the transfer line and the column, respectively, where d is the diameter thereof, L is the length thereof, and $\eta$ is the viscosity of the gas flowing therethrough.

In some embodiments, the sampling device adjusts the pressure of the carrier gas supplied to the column such that a substantially constant velocity is maintained in the column. In some of these embodiments, the pressure of the carrier gas supplied to the column is calculated in accordance with the equation $$\overline{u} = j \cdot \frac{4 \cdot a \cdot b}{\pi \cdot d_c^2 \cdot P_o} \cdot \frac{T_c}{T_t} \cdot \left[\frac{(P_i^2 - P_o^2)}{a \cdot \frac{T_c}{T_t} + b}\right]$$

where $\overline{u}$ is the velocity of the gas through the column, $T_t$ is the transfer line absolute temperature, $T_c$ is the column absolute temperature, $P_o$ is the gas pressure at the column outlet, $d_c$ is the diameter of the column, j is the compressibility factor for the gas, and a and b represent $\pi d/256L\eta$ for the transfer line and the column, respectively, where d is the diameter thereof, L is the length thereof, and $\eta$ is the viscosity of the gas flowing therethrough. In some of these embodiments, the compressibility factor j is calculated in accordance with the equation $$j = \frac{3}{2} \cdot \frac{\left(\frac{P_x^2}{P_o^2} - 1\right)}{\left(\frac{P_x^3}{P_o^3} - 1\right)}$$

where $P_x$ is the gas pressure at the column inlet, which is calculated in accordance with the equation $$P_x^2 = \frac{a \cdot \frac{T_c}{T_t} \cdot P_i^2 + b \cdot P_o^2}{a \cdot \frac{T_c}{T_t} + b}$$

In certain embodiments, the invention comprises a method for regulating fluid flowing through a chromatographic column, including providing a sampling device that supplies a carrier gas containing analytes to be measured, providing a chromatographic column that receives the carrier gas containing the analytes supplied by the sampling device, measuring the temperature of the column with a temperature sensor, sending a signal that indicates the measured temperature to the sampling device, calculating a pressure at which the carrier gas is supplied to the column based on the signal received by the sampling device, and supplying the carrier gas to the column at the calculated pressure.

In some embodiments, the steps of measuring the temperature, sending a signal, calculating a pressure, and supplying the carrier gas are repeated so as to supply the carrier gas to the column such that a substantially constant flow rate is maintained in the column.

In some embodiments, the steps of measuring the temperature, sending a signal, calculating a pressure and supplying the carrier gas are repeated so as to supply the carrier gas to the column such that a substantially constant velocity is maintained in the column.

In some embodiments, the temperature sensor is a platinum resistor thermometer. In other embodiments, the temperature sensor is a thermocouple.

In some embodiments, the sampling device is a thermal desorption unit. In certain embodiments, the invention further includes a transfer line assembly through which the carrier gas is communicated from the thermal desorption unit to the column and a signal cable by which the temperature sensor is connected to the sampling device, wherein the signal cable is bound into the transfer line assembly. In certain embodiments, the thermal desorption unit includes a removable sample vessel for obtaining a sample from an environment to be tested, a sample station positioned in the flow path of a carrier gas for receiving the sample vessel, and a heating device for heating the sample vessel in the sample station to thermally desorb the analytes therein.

In some embodiments, the sampling device is a headspace sampler.

DETAILED DESCRIPTION OF THE DRAWINGS

Figure 1:
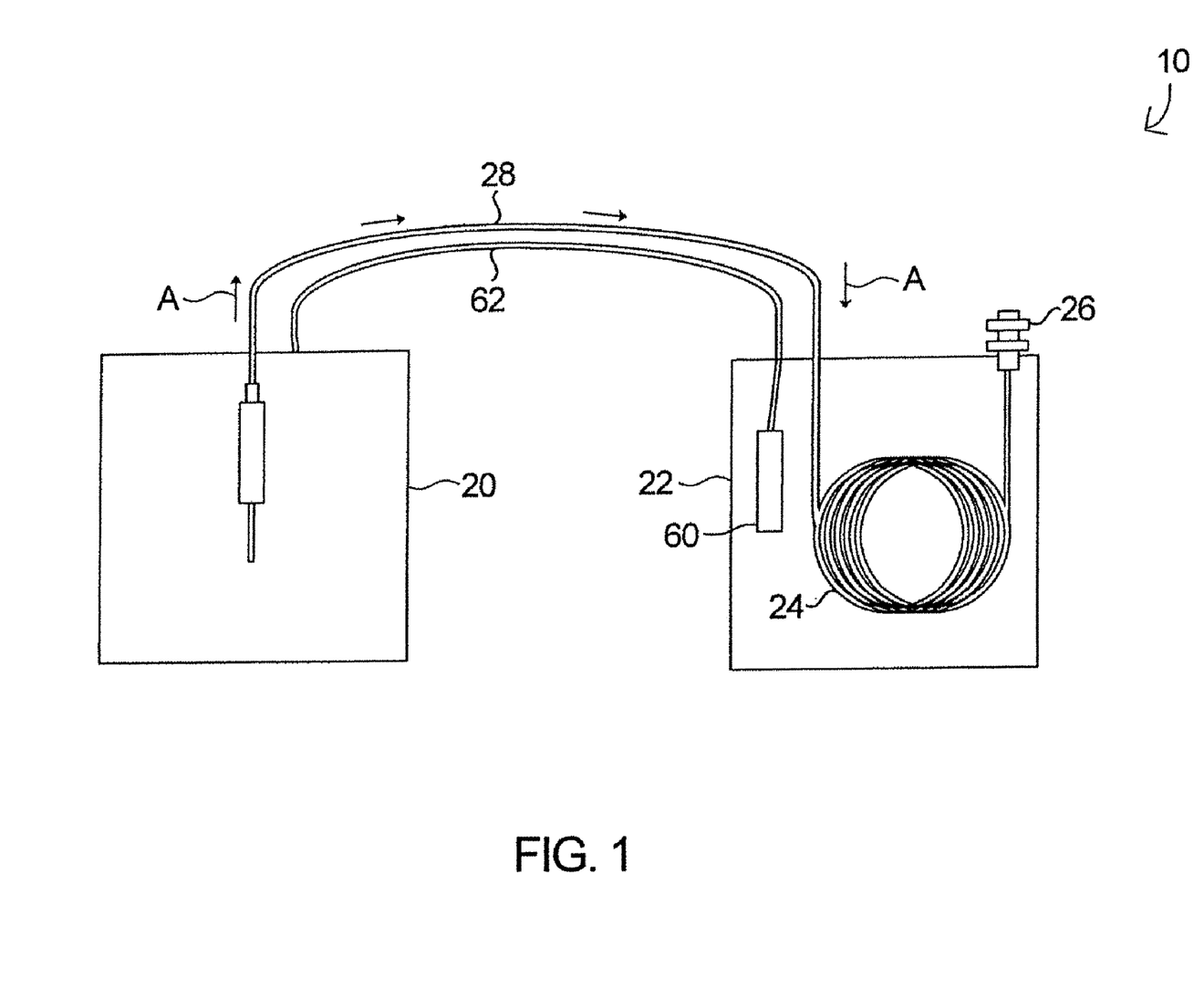
FIG. 1 is a schematic view of a system for regulating gas flowing through a chromatographic column in accordance with one embodiment of the invention.

The basic components of one embodiment of a chromatographic system 10 for measuring analytes in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention. The system 10 includes a sampling device 20, which, in the particular embodiment described below, is a thermal desorption unit, but, in other embodiments, may include other sampling devices, such as a headspace sampler. The system 10 further includes a gas chromatograph 22, which includes a chromatographic column 24 connected to a detector 26. The thermal desorption unit 20 is in fluid communication with the chromatograph 22 via a transfer line 28, through which a sample mixture is communicated from the unit 20 to the chromatograph 22 (indicated by arrows A), which may, for example, comprise a length of fused silica restrictor tubing.

The chromatograph 22 further includes a temperature sensor 60 for measuring the temperature of the column 24. The sensor 60 may, for example, be a platinum resistor thermometer, or may, as another example, be a thermocouple. The sensor 60 is connected to the thermal desorption unit 20 via a signal cable 62, through which a signal indicating the value of the column temperature can be communicated to the unit 20. In some embodiments, the signal cable 62 is bound into the transfer line assembly.

Figure 2A:
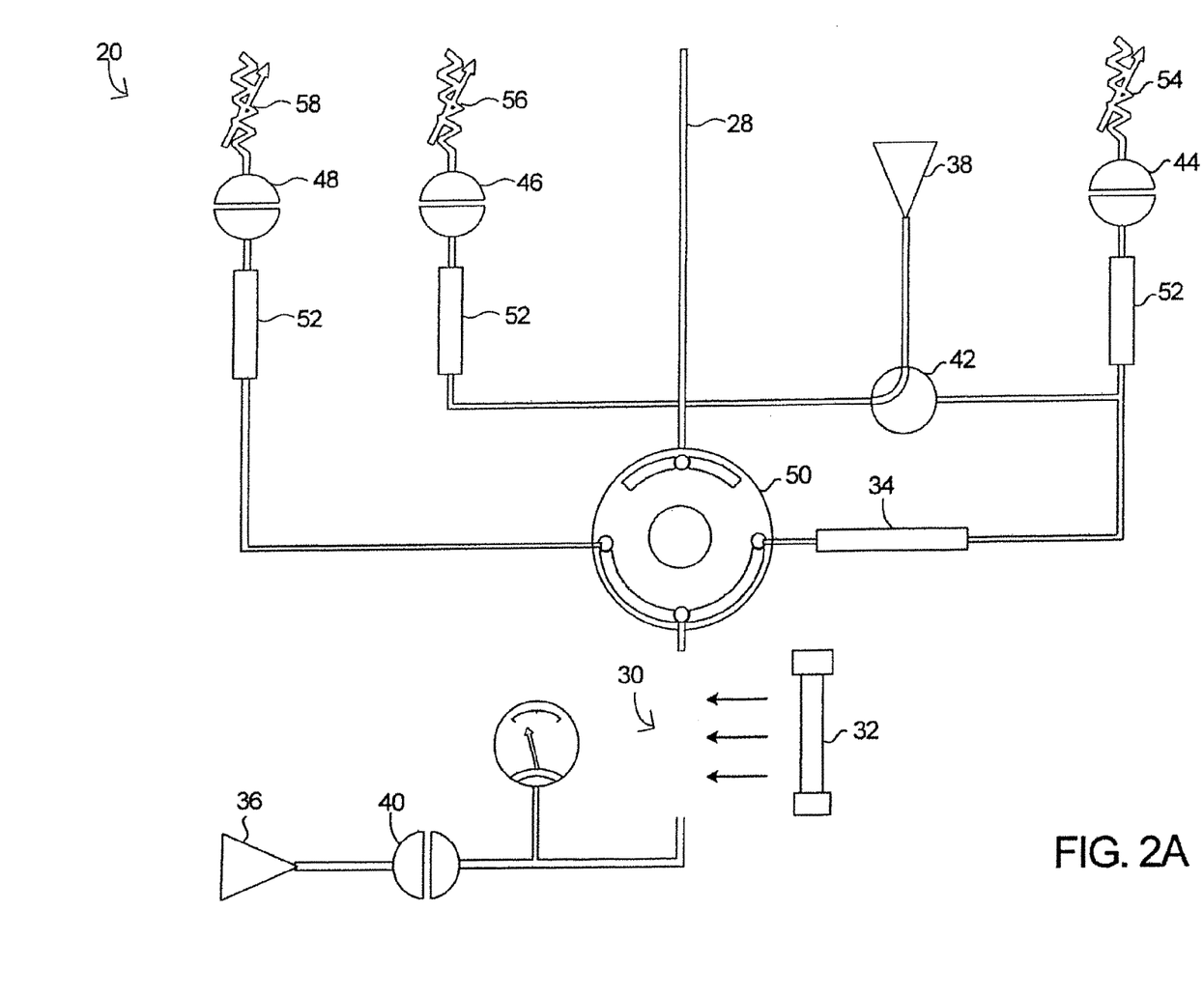
FIG. 2A is a schematic view showing additional detail of the system of FIG. 1.

As illustrated in FIG. 2A, the thermal desorption unit 20 generally comprises a sample station 30, in which a sample vessel 32, such as a sorbent tube, is disposed. In some embodiments, a trap 34, such as another sorbent tube, is placed downstream of the sample tube 32 for further preconcentration of the analytes. The tube 32, adsorbent trap 34, and transfer line 28 are selectively in communication with each other via a rotary valve 50. A carrier gas inlet 36 is selectively in fluid communication with the sample tube 32 via a valve 40, and another carrier gas inlet 38 is selectively in fluid communication with the adsorbent trap 34 via a valve 42. A desorb vent needle valve 54, an outlet split needle valve 56, and an inlet split needle valve 58 are controlled via solenoid valves 44, 46, 48, respectively, each of which is preceded by a charcoal trap 52.

Figure 2B:
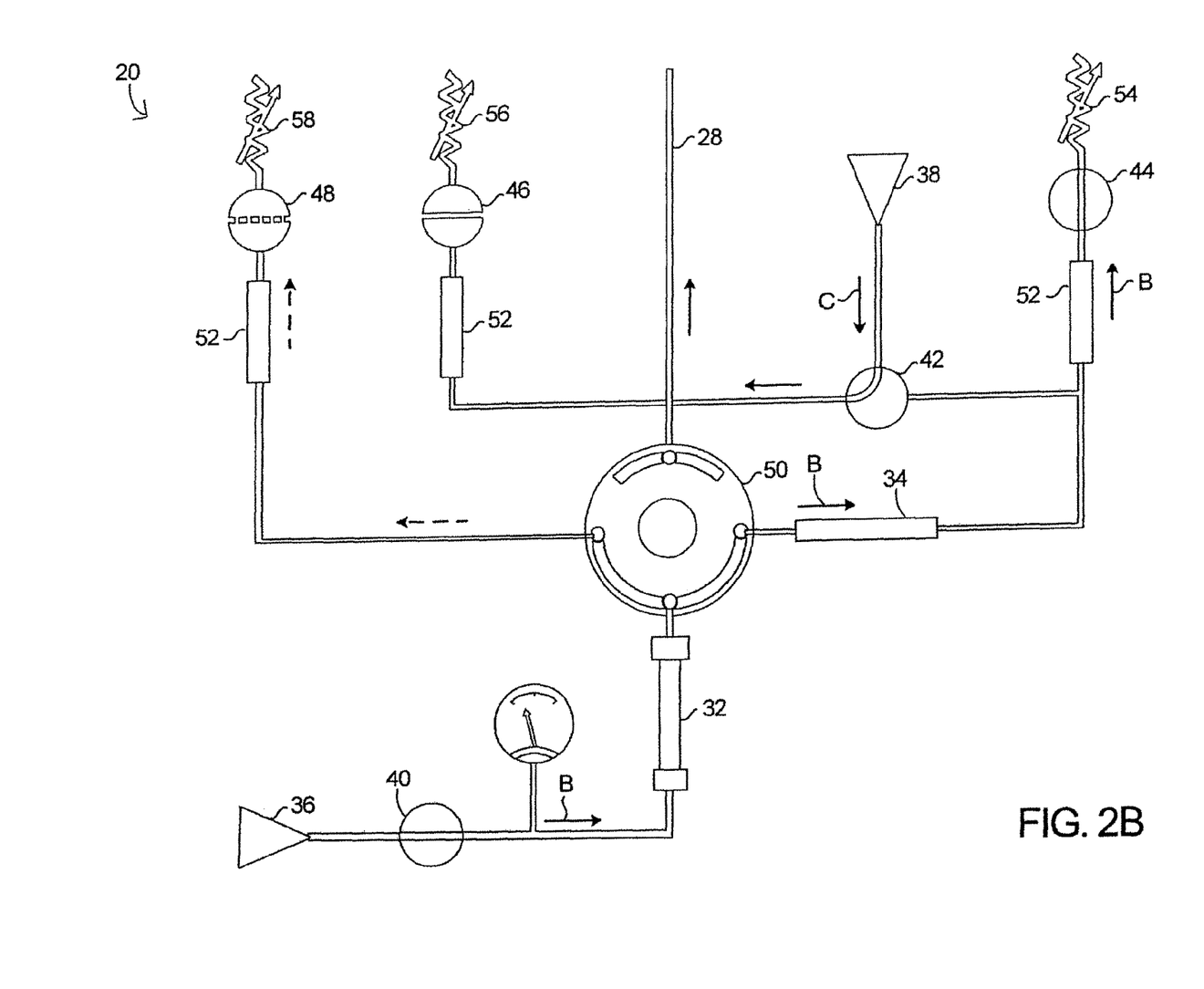
FIG. 2B is a schematic view showing additional detail of the system of FIG. 1 during a tube purge stage.

In operation, a sample tube 32, which contains the analytes obtained from the environment to be tested, is first disposed in the sample station 30 of the thermal desorption unit 20, as illustrated in FIG. 2A. As shown in FIG. 2B, with the rotary valve 50 positioned such that the sample tube 32 is in fluid communication with the trap 34, the valves 40, and 44 are opened. The tube 32 is heated in order to desorb the analytes therefrom, and carrier gas flows in through the inlet 36, through the tube 32, and sweeps the analytes into the trap 34.

Figure 2C:
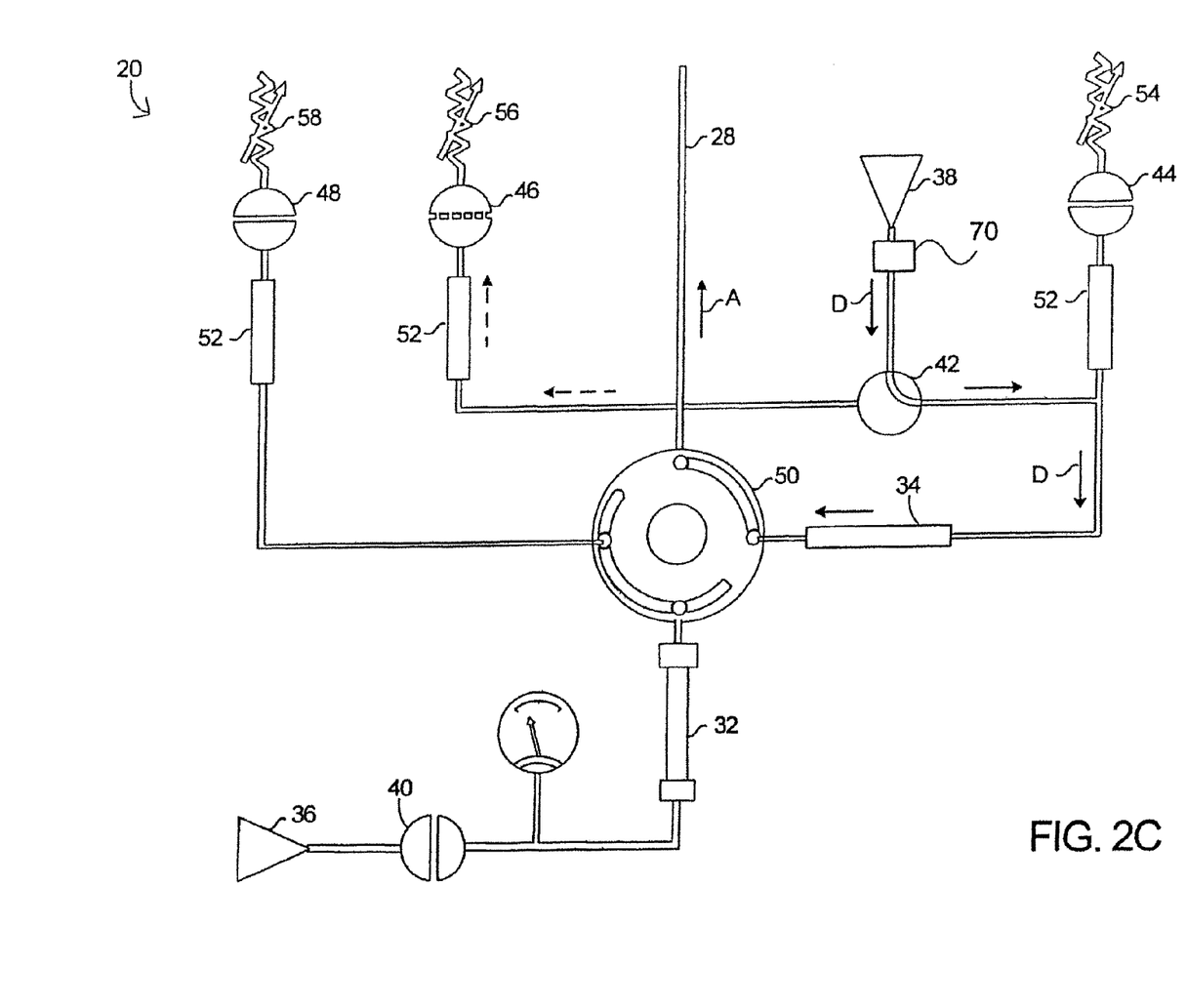
FIG. 2C is a schematic view showing additional detail of the system of FIG. 1 during a trap desorb stage.

An adsorbent disposed in the trap 34 adsorbs the analytes, and the carrier gas flows out through the valve 54 (indicated by arrows B). Subsequently, as shown in FIG. 2C, the rotary valve 50 is rotated such that the trap 34 is in fluid communication with the transfer line 28, the valves 40 and 44 are closed, and the direction of the valve 42 is switched to place the gas inlet 38 in communication with the trap 34. The trap 34 is heated in order to desorb the analytes therefrom, and carrier gas flows in through the inlet 38 and through the trap 34 (indicated by arrows D), where it sweeps the analytes out of the trap 34 and into the transfer line 28 (indicated by arrows A).

As shown in FIG. 1, the transfer line 28 communicates the gas to the chromatographic column 24, through which it flows in order to perform the separation of its constituents for subsequent analysis by the detector 26. As the column 24 is heated, the viscosity of the gas flowing therethrough increases, which would normally decrease the flow rate of the gas, which may impact detection performance.

Accordingly, the column temperature $T_c$ is monitored and used to change the pressure P at which the gas containing the analytes is supplied to the transfer line 28. This is accomplished by recognizing that the flow rate $F_o$ of the gas exiting the column 24 at the column outlet can be represented according to the following equation:

$$F_o = \frac{\pi \cdot d_c^4 \cdot (P^2 - P_o^2)}{256 \cdot L_c \cdot \eta_c \cdot P_o} \quad (1)$$

Where: $F_o$ is the flow rate at the column outlet $d_c$ is the internal diameter of the column $L_c$ is the length of the column $\eta_c$ is the viscosity of the carrier gas in the column P is the carrier gas pressure at the column inlet $P_o$ is the carrier gas pressure at the column outlet When using a temperature programmed column where the carrier gas is applied to the column inlet at a constant pressure, the only variable that will alter so as to change the flow rate $F_o$ at the column outlet is the viscosity $\eta_c$ of the gas flowing through the column, which will increase as the temperature of the column is increased. Therefore, a corresponding increase in inlet pressure P can be applied at the column inlet as the viscosity $\eta_c$ increases, thereby allowing a constant flow rate $F_o$ at the column outlet to be maintained.

The viscosity varies with respect to changes in temperature in a relatively predictable manner for the common carrier gases. This relationship between viscosity and temperature can be approximated according to the following equation:

$$\eta_c = \eta_0 \left(\frac{T_c}{T_0}\right)^x \quad (2)$$

Where: $\eta_c$ is the viscosity at column temperature $T_c$ $\eta_0$ is the viscosity at absolute temperature $T_0$ (from published tables)

x is a dimensionless constant

The coefficients for the three most common carrier gases, for example, are provided in the following table:

TABLE 1

| Gas | $T_0$ (K) | $\eta_0$ (Pa·s × $10^{-6}$) | x |
|---|---|---|---|
| Hydrogen | 273.2 | 8.399 | 0.680 |
| Nitrogen | 273.2 | 16.736 | 0.725 |
| Helium | 273.2 | 18.662 | 0.646 |

Accordingly, by determining the column temperature $T_c$, one can determine the viscosity $\eta_c$ using Equation 2 and Table 1. The viscosity $\eta_c$ can then be used with Equation 1 to determine the value of P at the column inlet necessary to maintain a required flow rate $F_o$ at the column outlet by employing a suitable algorithm such as successive approximation.

When using a system that employs a sampling device 20 connected to the column 24 via a transfer line 28, the transfer line must also be taken into account. Typically, the geometry (length and diameter) of the transfer line 28 will differ from that of the column. Accordingly, a combined function will be required to determine the relative values of this serially connected system, as described below.

As with Equation 1, the flow rate $F_t$ of the gas exiting the transfer line 28 at the transfer line outlet can be represented according to the following equation:

$$F_t = \frac{\pi \cdot d_t^4 \cdot (P_i^2 - P_x^2)}{256 \cdot L_t \cdot \eta_t \cdot P_x} \tag{3}$$

Where: $F_t$ is the flow rate at the transfer line outlet
  $d_t$ is the internal diameter of the transfer line
  $L_t$ is the length of the transfer line
  $\eta_t$ is the viscosity of the carrier gas in the transfer line
  $P_i$ is the carrier gas pressure at the transfer line inlet
  $P_x$ is the carrier gas pressure at the transfer line outlet The flow rate $F_i$ of the gas entering the column 24 at the column inlet can be represented according to the following equation:

$$F_i = \frac{\pi \cdot d_c^4 \cdot (P^2 - P_o^2)}{256 \cdot L_c \cdot \eta_c \cdot P} \tag{4}$$

However, because the transfer line 28 is connected directly to the column 24, the gas pressure P at the column inlet is the same as the gas pressure $P_x$ at the transfer line outlet, and thus, Equation 4 can be represented as follows:

$$F_i = \frac{\pi \cdot d_c^4 \cdot (P_x^2 - P_o^2)}{256 \cdot L_c \cdot \eta_c \cdot P_x} \tag{5}$$

By substituting a for $$\frac{\pi \cdot d_t^4}{256 \cdot L_t \cdot \eta_t}$$

and b for $$\frac{\pi \cdot d_c^4}{256 \cdot L_c \cdot \eta_c},$$

Equations 3 and 5 can be replaced with Equations 6 and 7, respectively, as follows:

$$F_t = a \cdot \frac{P_i^2 - P_x^2}{P_x} \tag{6}$$

$$F_i = b \cdot \frac{P_x^2 - P_o^2}{P_x} \tag{7}$$

Again, because the transfer line 28 is connected directly to the column 24, the gas eluting from the line 28 and the gas entering the column 24 will have the same pressure, and therefore, will have the same mass flow. However, because they will have different temperatures, they will have different volumetric flows, which must be accounted for. This relationship is represented in the following equation:

$$F_i = \frac{T_c}{T_t} \cdot F_t \tag{8}$$

Where: $T_c$ is the column absolute temperature
  $T_t$ is the transfer line absolute temperature Using Equation 8 in Equation 6 yields the following equation:

$$F_i = a \cdot \frac{P_i^2 - P_x^2}{P_x} \cdot \frac{T_c}{T_t} \tag{9}$$

Combining Equation 9 with Equation 7 then yields the following Equation:

$$a \cdot \frac{P_i^2 - P_x^2}{P_x} \cdot \frac{T_c}{T_t} = b \cdot \frac{P_x^2 - P_o^2}{P_x} \tag{10}$$

Equation 10, can then be reduced as follows:

$$a \cdot \frac{T_c}{T_t} \cdot P_i^2 - a \cdot \frac{T_c}{T_t} \cdot P_x^2 = b \cdot P_x^2 - b \cdot P_o^2 \tag{11}$$

$$a \cdot \frac{T_c}{T_t} \cdot P_i^2 + b \cdot P_o^2 = P_x^2 \cdot \left( a \cdot \frac{T_c}{T_t} + b \right) \tag{12}$$

$$P_x^2 = \frac{a \cdot \frac{T_c}{T_t} \cdot P_i^2 + b \cdot P_o^2}{a \cdot \frac{T_c}{T_t} + b} \tag{13}$$

By substituting b into Equation 1, the flow rate $F_o$ at the column outlet can be represented as follows:

$$F_o = b \cdot \frac{P_x^2 - P_o^2}{P_o} \tag{14}$$

Equations 13 and 14 can then be combined to produce Equations 15 through 18, below:

$$F_o = \frac{b}{p_o} \cdot \left[ \frac{a \cdot \frac{T_c}{T_t} \cdot P_i^2 + b \cdot P_o^2}{a \cdot \frac{T_c}{T_t} + b} - P_o^2 \right] \quad (15)$$

$$F_o = \frac{b}{p_o} \cdot \left[ \frac{a \cdot \frac{T_c}{T_t} \cdot P_i^2 + b \cdot P_o^2 - a \cdot \frac{T_c}{T_t} \cdot P_o^2 - b \cdot P_o^2}{a \cdot \frac{T_c}{T_t} + b} \right] \quad (16)$$

$$F_o = \frac{a \cdot b}{p_o} \cdot \frac{T_c}{T_t} \cdot \left[ \frac{(P_i^2 - P_o^2)}{a \cdot \frac{T_c}{T_t} + b} \right] \quad (17)$$

The column outlet will normally be at an elevated temperature and possibly at a pressure different from ambient. It is normal practice to express (and apply) the flow rate corrected to Standard Ambient Temperature and Pressure (SATP), as shown below:

$$F_a = F_o \frac{T_a}{T_c} \cdot \frac{P_o}{P_a} \quad (18)$$

Where: $F_a$ is the flow rate at the column outlet (corrected to SATP)
$T_a$ is the standard ambient absolute temperature (298.15 K)
$P_a$ is the standard ambient pressure (100 kPa)
Substituting Equation 18 into Equation 17 produces Equations 19 and 20, below:

$$F_a = a \cdot b \cdot \frac{T_a}{T_t \cdot P_a} \cdot \left[ \frac{(P_i^2 - P_o^2)}{a \cdot \frac{T_c}{T_t} + b} \right] \quad (19)$$

$$P_i = \sqrt{\frac{F_a \cdot T_t \cdot P_a}{a \cdot b \cdot T_a} \cdot \left( a \cdot \frac{T_c}{T_t} + b \right) + P_o^2}. \quad (20)$$

Equation 20 may be employed to calculate the pressure $P_i$ at the transfer line inlet to maintain a constant flow rate $F_a$ at the column outlet. During a column temperature program, only the values of $T_c$ and b will change, and therefore, the remaining values may be calculated in advance of the chromatographic analysis in order to reduce processing time.

Accordingly, in operation, the temperature sensor 60 measures the column temperature $T_c$ and sends a signal reflecting this value to the thermal desorption unit 20 via the signal line 62. The unit 20 then uses this value to calculate the pressure $P_i$ at which it applies the carrier gas to the inlet of the transfer line 28 in accordance with Equation 20. Once the pressure $P_i$ is calculated, the unit 20 uses a pressure regulator 70 or other appropriate device to adjust the pressure $P_i$ applied to the transfer line 28. By adjusting the pressure $P_i$ in this way, a constant flow through the column 24 can be maintained.

Figure 2D:
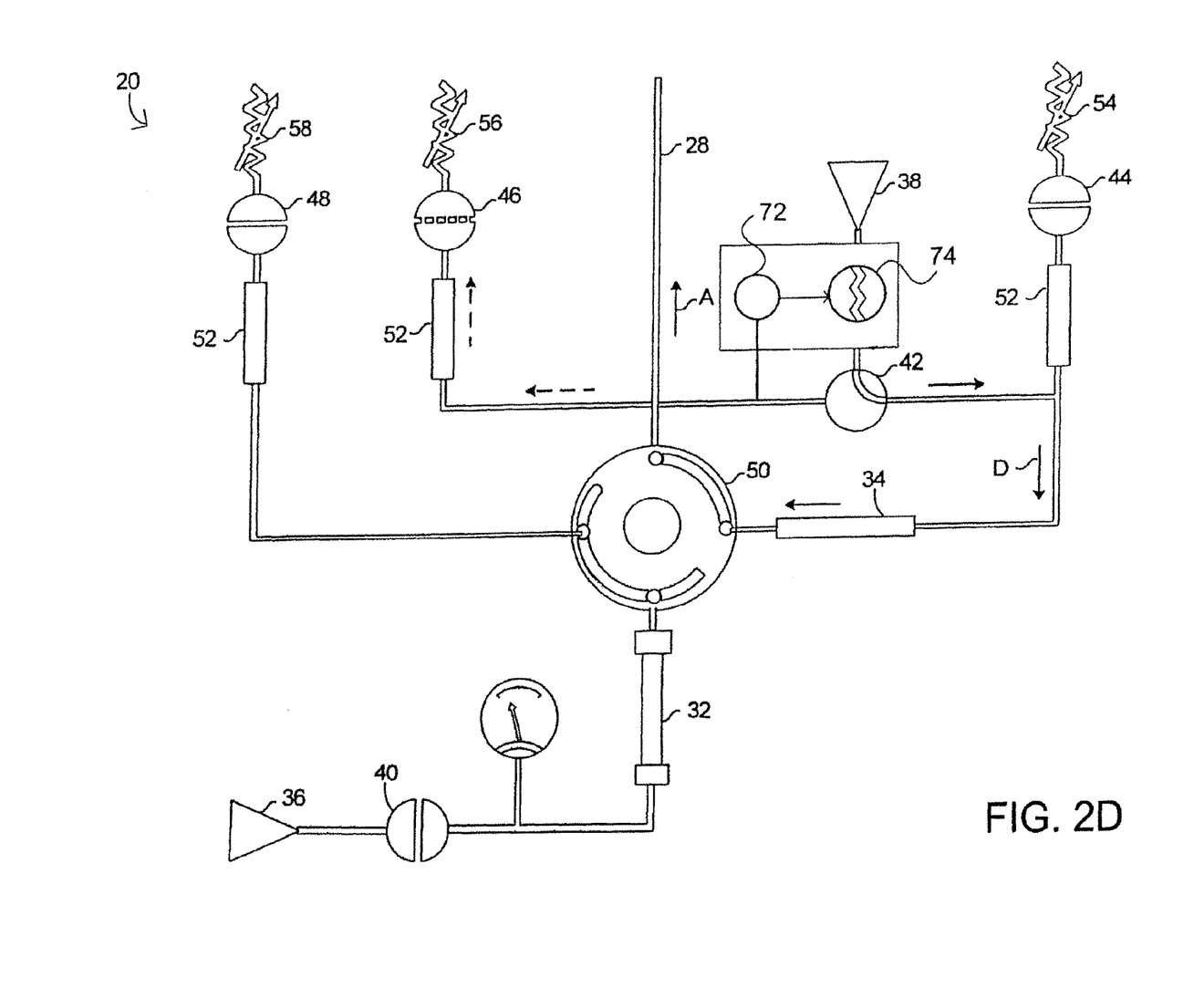
FIG. 2D is a schematic view showing additional detail of the system of 1 during the trap desorb stage.

As illustrated in FIG. 2D, in some embodiments, a proportional valve 74 is employed in order to compensate for a pressure drop that may occur across the trap 34. In these embodiments, a pressure transducer 72 measures the pressure of the gas entering the transfer line 28 from the valve 50 and, if the pressure is lower than the pressure of the gas entering through gas inlet 38, adjusts the valve 74 to increase the pressure upstream of the trap 34 to compensate for this pressure drop.

Similarly, the temperature $T_c$ can be monitored and used to calculate the pressure at which the unit 20 should apply the carrier gas containing the analytes to the transfer line 28 in order to maintain a constant velocity of the gas flowing through the column 24. This can be achieved by recognizing that the velocity of a gas through a column, which is normally expressed as the mean gas velocity, is related to the outlet flow rate (at the temperature and pressure applied there). Additionally, because the gas is compressible, the Martin and James compressibility factor can be applied, resulting in the following representation of gas velocity:

$$\bar{u} = j \cdot \frac{4 \cdot F_o}{\pi \cdot d_c^2} \quad (21)$$

Where: u is the mean carrier gas velocity through the column
j is the compressibility factor
Using Equation 17 in equation 21 results in the following representation of the mean gas velocity for a particular applied pressure $P_i$.

$$\bar{u} = j \cdot \frac{4 \cdot a \cdot b}{\pi \cdot d_c^2 \cdot P_o} \cdot \frac{T_c}{T_t} \cdot \left[ \frac{(P_i^2 - P_o^2)}{a \cdot \frac{T_c}{T_t} + b} \right] \quad (22)$$

Equation 22 can be rearranged to represent the required pressure $P_i$ (like Equation 20) as follows:

$$P_i = \sqrt{\frac{\pi \cdot \bar{u} \cdot d_c^2 \cdot P_o \cdot T_t}{4 \cdot j \cdot a \cdot b \cdot T_c} \cdot \left( a \cdot \frac{T_c}{T_t} + b \right) + P_o^2} \quad (23)$$

However, computation would be very complex because of the presence of the compressibility factor j in this equation. This results from the fact that the compressibility factor j is represented as follows:

$$j = \frac{3}{2} \cdot \frac{\left( \frac{P_x^2}{P_o^2} - 1 \right)}{\left( \frac{P_x^3}{P_o^3} - 1 \right)} \quad (24)$$

and the value of $P_x$ is obtained using $P_i$ as a parameter, as shown in Equation 13.

Therefore, an alternative computational approach is to use numeric methods to solve Equation 22. For example, a successive approximation method may be employed to optimize the value of $P_i$ in order to achieve a target gas velocity.

Accordingly, in operation, the temperature sensor 60 measures the column temperature $T_c$ and sends a signal reflecting this value to the thermal desorption unit 20. A pressure $P_i$ is selected, and a velocity $\bar{u}$ of the gas through the column 24 is calculated in accordance with Equation 22. This is iterated to determine the pressure $P_i$ that produces the most uniform value of the velocity $\bar{u}$ as the temperature changes. The pressure regulator in the unit 20 then regulates the pressure $P_i$ of the gas applied to the inlet of the transfer line 28, thereby maintaining a constant gas velocity in the column 24.

Though the aforementioned example has been described with respect to a transfer line connected in series with a column in order to communicate fluid from a sampling device to a column, the system of the present invention is also applicable to other chromatographic applications involving serial connections of fluid conduits such as columns and/or transfer lines.

Figure 3:
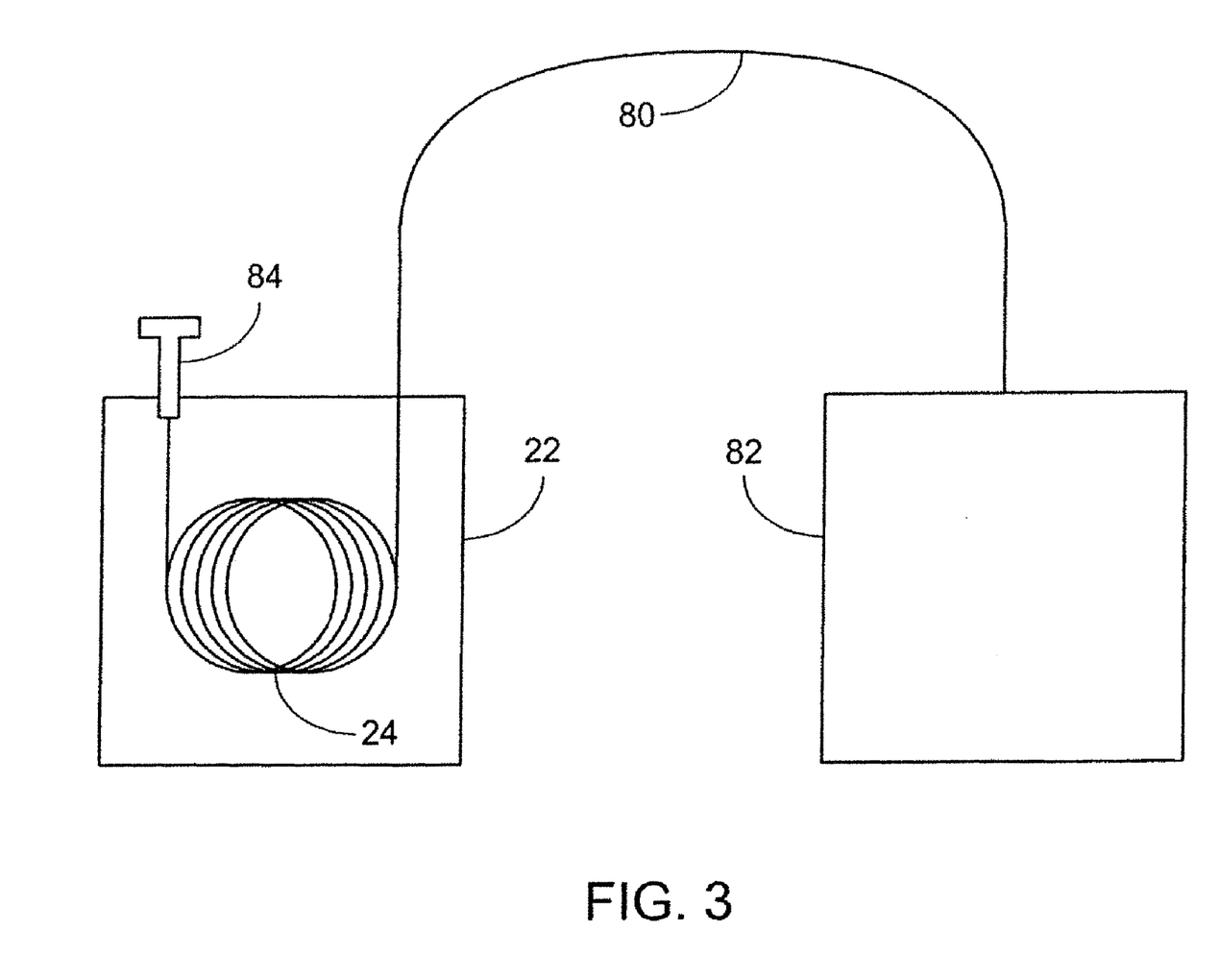
FIG. 3 is a schematic view of the system of FIG. 1 with a transfer line connected downstream of a column.

For example, as illustrated in FIG. 3, the transfer line 80 may be employed to communicate fluid from the outlet of the column 24 to an external detection system 82, such as, for example, a mass spectrometer, or, as another example, a Fourier-transform infrared spectrometer. The same flow, pressure, and velocity equations can be applied to govern the fluid exiting the transfer line 80, where $P_i$ represents the pressure of the system inlet (in this case, the inlet of the column 24), and $P_o$ represents the pressure at the system outlet (in this case, the outlet of the transfer line 80). Using Equation 20, the pressure $P_i$ can be calculated and applied at the column inlet, which can be controlled, for example, by a chromatographic injector 84.

Similarly, flow and velocity can also be controlled for systems employing more than two fluid conduits that are serially connected. This can be more easily seen by first rewriting Equations 19 and 20, without abbreviations a and b, as Equations 25 and 26, respectively:

$$F_a = \frac{\pi \cdot T_a}{256 \cdot p_a} \cdot \frac{(p_i^2 - p_o^2)}{\left(\frac{T_t \cdot \eta_t \cdot L_t}{d_t^4}\right) + \left(\frac{T_c \cdot \eta_c \cdot L_c}{d_c^4}\right)} \quad (25)$$

$$p_i = 16 \cdot \sqrt{\frac{F_a \cdot p_a}{\pi \cdot T_a} \cdot \left[\left(\frac{T_t \cdot \eta_t \cdot L_t}{d_t^4}\right) + \left(\frac{T_c \cdot \eta_c \cdot L_c}{d_c^4}\right)\right] + p_o^2} \quad (26)$$

Figure 4:
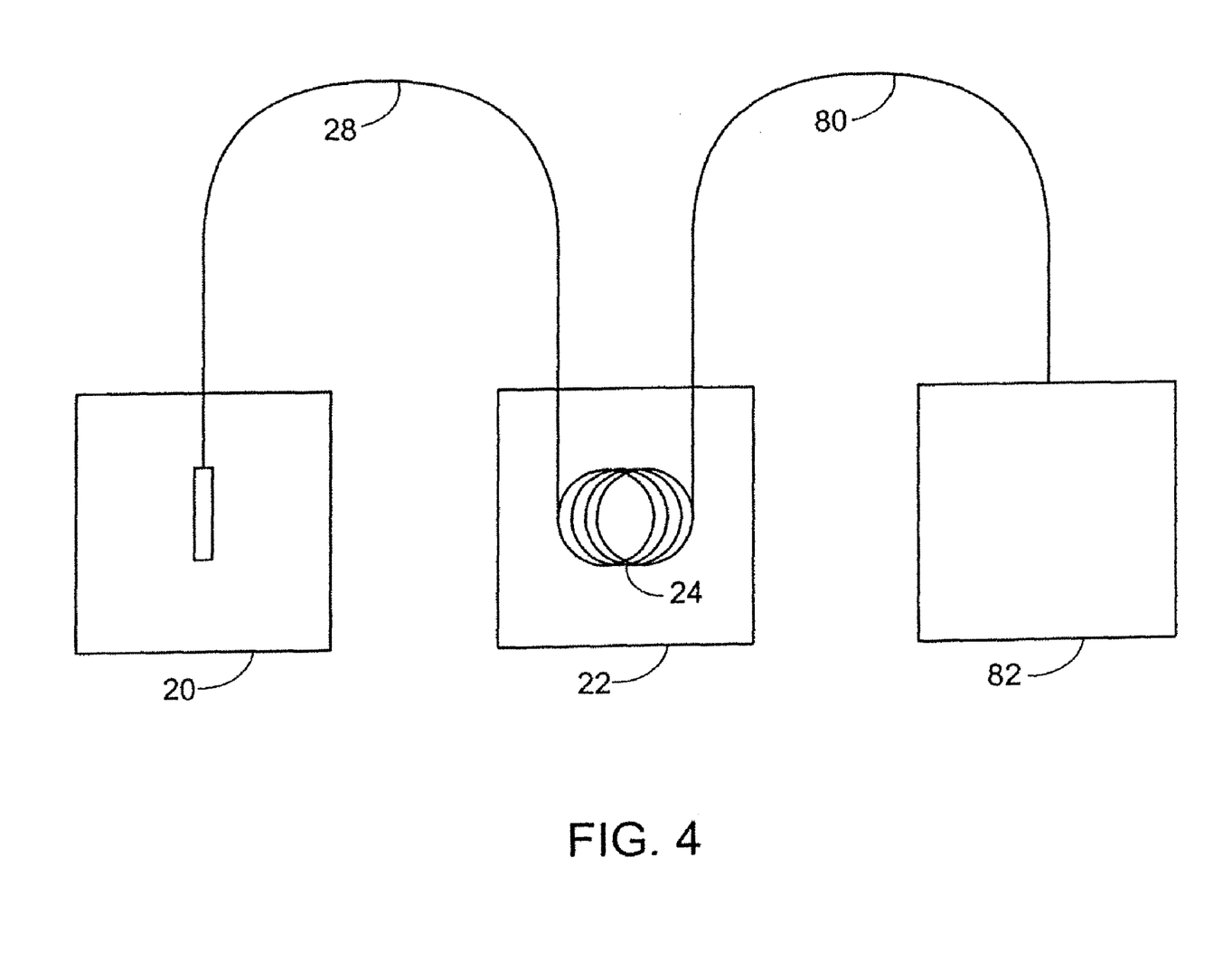
FIG. 4 is a schematic view of the system of FIG. 1 with transfer lines connected upstream and downstream of the column.

Referring to FIG. 4, an example of more than two fluid conduits serially connected is illustrated. A transfer line 28 communicates fluid from the thermal desorption unit 20 to the column 24, and the detector transfer line 80 communicates fluid from the column 24 to the detection system 82. Accordingly, the transfer line 28, column 24, and detector transfer line 82 are connected in series. In order to account for this third conduit, Equation 25 becomes Equation 27 as follows:

$$F_a = \frac{\pi \cdot T_a}{256 \cdot p_a} \cdot \frac{(p_i^2 - p_o^2)}{\left(\frac{T_t \cdot \eta_t \cdot L_t}{d_t^4}\right) + \left(\frac{T_c \cdot \eta_c \cdot L_c}{d_c^4}\right) + \left(\frac{T_d \cdot \eta_d \cdot L_d}{d_d^4}\right)} \quad (27)$$

where: $T_d$ is the temperature of the detector transfer line $n_d$ is the viscosity of the carrier gas in the detector transfer line at temperature Td $L_d$ is the length of the detector transfer line $d_d$ is the internal diameter of the detector transfer line Accordingly, solving for $P_i$ results in the following representation of the pressure to be applied at the system inlet (in this case, the inlet of transfer line 28):

$$p_i = 16 \cdot \sqrt{\frac{F_a \cdot p_a}{\pi \cdot T_a} \cdot \left[\left(\frac{T_t \cdot \eta_t \cdot L_t}{d_t^4}\right) + \left(\frac{T_c \cdot \eta_c \cdot L_c}{d_c^4}\right) + \left(\frac{T_d \cdot \eta_d \cdot L_d}{d_d^4}\right)\right] + p_o^2} \quad (28)$$

Figure 5:
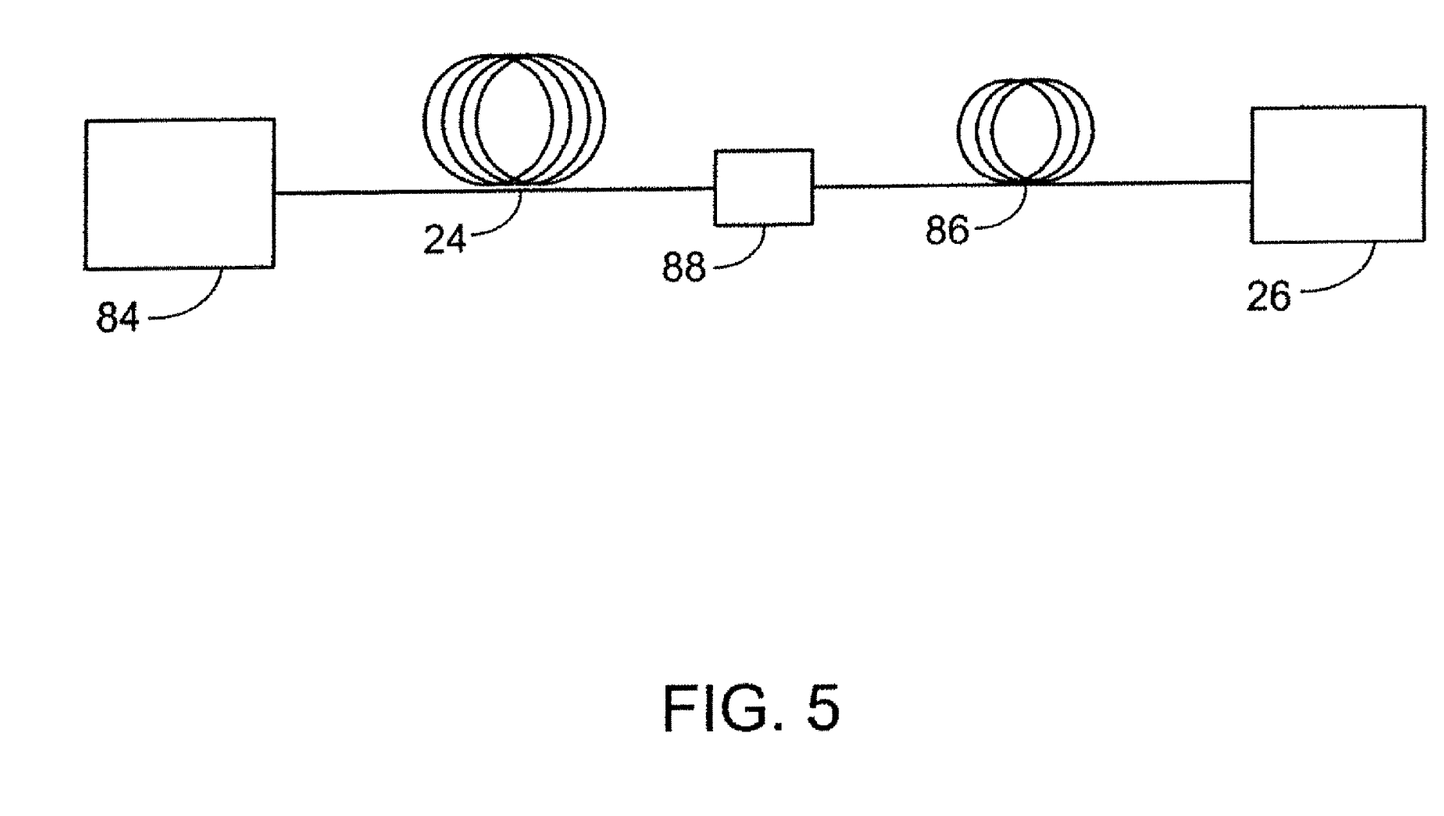
FIG. 5 is a schematic view of the system of FIG. 1 employing a second column instead of a transfer line.

Similarly, the above methods can be used in applications employing serially connected columns. For example, one such application is that of comprehensive two-dimensional (or multi-dimensional) gas chromatography. As illustrated in FIG. 5, these applications typically employ a second column 86 that is coupled to the first column 24 via a thermal modulator 88. In these applications, the modulator 88 repeatedly samples the fluid from the first column 24 and injects a pulse into the second column 86, which includes a stationary phase different than the first column 24. As a result, the analytes are separated according to different chemical properties (such as volatility and polarity) in the different columns. In these applications, or similar column-to-column applications, the variables described in the equations above relating to the properties of the transfer line 28 and column 24 can likewise be applied to the first column 24 and second column 86.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A system for regulating fluid flowing through a chromatographic column, comprising:
    a thermal desorption unit that supplies a carrier gas containing analytes to be measured, the thermal desorption unit including
        a removable sample vessel for obtaining a sample from an environment to be tested,
        a carrier gas inlet in fluid communication with the sample vessel via a solenoid valve,
        a sample station positioned in the flow path of a carrier gas for receiving the sample vessel,
        a heating device for heating the sample vessel in the sample station to thermally desorb the analytes therein
        a trap placed downstream of the sample vessel, and
        a second carrier gas inlet in fluid communication with the trap via a second valve; and
    a gas chromatograph in fluid communication with said thermal desorption unit, said gas chromatograph comprising
        a chromatographic column that receives the carrier gas containing the analytes supplied by said thermal desorption unit; and
        a temperature sensor connected to said thermal desorption unit that measures the temperature of said column and sends a signal to said thermal desorption unit indicating the measured temperature, said temperature sensor being a platinum resistor thermometer or a thermocouple;
    a transfer line assembly through which the carrier gas is communicated from the thermal desorption unit to said column;
    a signal cable by which said temperature sensor is connected to said thermal desorption unit, the signal cable being bound into the transfer line assembly; and
    a rotary valve,
    wherein the removable sample vessel, trap and transfer line assembly are selectively in communication with each other via the rotary valve,
    wherein said thermal desorption unit controls the pressure of the carrier gas supplied to said column based on the signal received from said sensor,
    wherein said thermal desorption unit adjusts the pressure of the carrier gas supplied to said column such that a substantially constant flow rate and a substantially constant velocity is maintained in said column, and wherein the pressure of the carrier gas supplied to the column is calculated in accordance with the equation $$P_i = \sqrt{\frac{F_a \cdot T_t \cdot P_a}{a \cdot b \cdot T_a} \cdot \left(a \cdot \frac{T_c}{T_t} + b\right) + P_o^2}$$

where $T_t$ is the transfer line absolute temperature, $T_c$ is the column absolute temperature, $T_a$ is the standard ambient absolute temperature, $P_o$ is the gas pressure at the column outlet, $P_a$ is the standard ambient pressure, and a and b represent $\pi d/256L\eta$ for the transfer line and the column, respectively, where d is the diameter thereof, L is the length thereof, and $\eta$ is the viscosity of the gas flowing therethrough.

2. The system of claim 1, wherein the thermal desorption unit further comprises a desorb vent needle valve controlled by a solenoid valve, a outlet split needle valve controlled by a solenoid valve, and an inlet split needle valve controlled by a solenoid valve.

3. The system of claim 1, further comprising a pressure regulator to adjust the pressure to the transfer line.

4. The system of claim 1, further comprising a pressure transducer for measuring the pressure of the carrier gas entering the transfer line assembly, and if the pressure is lower than the pressure of the gas entering the gas inlet, the pressure transducer adjusts the valve to increase the pressure upstream of the trap to compensate for the pressure drop in the transfer line assembly.

5. The system of claim 1, further comprising a detector transfer line and a detection system, where the detector transfer line communicates fluid from the column to the detection system.

6. The system of claim 5, wherein the transfer line, column, and detector transfer line are connected in series.

7. The system of claim 1, further comprising a second column coupled to the column by a thermal modulator.

8. The system of claim 7, wherein the thermal modulator repeatedly samples the fluid from the column and injects a pulse into the second column, whereby the analytes are separated according to different chemical properties in the column and the second column.

9. A method for regulating fluid flowing through a chromatographic column, the method comprising:
providing a thermal desorption unit that supplies a carrier gas containing analytes to be measured, the thermal desorption unit including:
a removable sample vessel for obtaining a sample from an environment to be tested,
a carrier gas inlet in fluid communication with the sample vessel via a solenoid valve,
a sample station positioned in the flow path of a carrier gas for receiving the sample vessel,
a heating device for heating the sample vessel in the sample station to thermally desorb the analytes therein
a trap placed downstream of the sample vessel, and
a second carrier gas inlet in fluid communication with the trap via a second valve;
providing a chromatographic column that receives the carrier gas containing the analytes supplied by the thermal desorption unit;
providing a transfer line assembly through which the carrier gas is communicated from the thermal desorption unit to the column, wherein the step of sending a signal comprises sending a signal via a signal cable bound into the transfer line assembly and connected to the thermal desorption unit;
measuring the temperature of the column with a temperature sensor, the temperature sensor being a platinum resistor thermometer or a thermocouple;
sending a signal that indicates the measured temperature to the thermal desorption unit;
calculating a pressure at which the carrier gas is supplied to the column based on the signal received by the thermal desorption unit; and
supplying the carrier gas to the column at the calculated pressure,
wherein the steps of measuring the temperature, sending a signal, calculating a pressure and supplying the carrier gas are repeated so as to supply the carrier gas to the column such that a substantially constant flow rate and a substantially constant velocity are maintained in the column, wherein the pressure of the carrier gas supplied to the column is calculated in accordance with the equation $$P_i = \sqrt{\frac{F_a \cdot T_t \cdot P_a}{a \cdot b \cdot T_a} \cdot \left(a \cdot \frac{T_c}{T_t} + b\right) + P_o^2}$$

where $T_t$ is the transfer line absolute temperature, $T_c$ is the column absolute temperature, $T_a$ is the standard ambient absolute temperature, $P_o$ is the gas pressure at the column outlet, $P_a$ is the standard ambient pressure, and a and b represent $\pi d/256L\eta$ for the transfer line and the column, respectively, where d is the diameter thereof, L is the length thereof, and $\eta$ is the viscosity of the gas flowing therethrough.

* * * * *